(12) United States Patent
Jorgenson et al.

(10) Patent No.: US 12,334,603 B2
(45) Date of Patent: *Jun. 17, 2025

(54) SYSTEM TO STERILIZE A PHYSICAL SPACE

(71) Applicant: BWR Innovations LLC, Fargo, ND (US)

(72) Inventors: Joel A. Jorgenson, Fargo, ND (US); Martha S. Kearns, Fargo, ND (US); Adam C. Jorgenson, West Fargo, ND (US); Brian C. Messerschmidt, Glyndon, MN (US); Thomas S. Wohl, West Fargo, ND (US)

(73) Assignee: BWR Innovations LLC, West Fargo, ND (US)

( * ) Notice: Subject to any disclaimer, the term of this patent is extended or adjusted under 35 U.S.C. 154(b) by 175 days.

This patent is subject to a terminal disclaimer.

(21) Appl. No.: 18/297,795

(22) Filed: Apr. 10, 2023

(65) Prior Publication Data

US 2023/0307671 A1    Sep. 28, 2023

Related U.S. Application Data

(63) Continuation of application No. 17/985,334, filed on Nov. 11, 2022, now Pat. No. 11,626,599, which is a
(Continued)

(51) Int. Cl.
*H01M 8/04*    (2016.01)
*A01M 1/20*    (2006.01)
(Continued)

(52) U.S. Cl.
CPC ...... *H01M 8/04089* (2013.01); *A01M 1/2094* (2013.01); *A61L 2/06* (2013.01);
(Continued)

(58) Field of Classification Search
None
See application file for complete search history.

(56) References Cited

U.S. PATENT DOCUMENTS

| | | |
|---|---|---|
| 2007/0193999 A1 | 8/2007 | Peterson |
| 2013/0183749 A1 | 7/2013 | Aamodt |
| 2019/0321500 A1 | 10/2019 | Anderson |

OTHER PUBLICATIONS http://www.altergy.com/products-2/mobile-solutions/; Altergy Mobile Solutions Webpage; Received Aug. 28, 2019.
(Continued)

*Primary Examiner* — Jelitza M Perez
(74) *Attorney, Agent, or Firm* — Neustel Law Offices

(57) ABSTRACT

A system for sterilizing a physical space, such as a hotel room. The system generates and distributes heated air to the physical space to elevate the temperature of the space to a level sufficient to achieve a desired sterilization effect of eradicating insects and microorganisms. The system is portable and self-contained. The system includes a hydrogen fuel cell that generates electrical power. An electrical system conditions and stores the electrical power and supplies stored electrical power to the system components and peripherals. System components include a source of hydrogen, a heater, an air distributor, and a filter. Peripherals include a UV light source and an aerosol dispenser. The combination of heat, UV light and aerosol disinfectant effectively eradicates insects, microorganisms, allergens, and odors in the physical space.

20 Claims, 7 Drawing Sheets

Related U.S. Application Data continuation of application No. 17/493,429, filed on Oct. 4, 2021, now Pat. No. 11,502,314, which is a continuation of application No. 16/553,532, filed on Aug. 28, 2019, now Pat. No. 11,139,488.

(60) Provisional application No. 62/723,789, filed on Aug. 28, 2018.

(51) Int. Cl.
| | |
|---|---|
| *A61L 2/06* | (2006.01) |
| *A61L 2/10* | (2006.01) |
| *A61L 2/16* | (2006.01) |
| *H01M 8/04082* | (2016.01) |
| *H01M 8/04089* | (2016.01) |

(52) U.S. Cl.
CPC .................................... *A61L 2/10* (2013.01); *A61L 2/16* (2013.01); *H01M 8/04201* (2013.01); *A01M 2200/01* (2013.01)

(56) References Cited

OTHER PUBLICATIONS http://www.altergy.com/products-2/enclosures/; Altergy Enclosures Webpage; Received Aug. 28, 2019.
http://www.altergy.com/wp-content/uploads/2018/07/Altergy_TSP_Data_sheet_2018_ATP_web.pdf, Altergy Traffic Signal Platform (TSP) Data Sheet; Published 2018.
http://www.altergy.com/wp-content/uploads/2017/09/Altergy_Reformer_Data_sheet_7_ATP_web.pdf, Altergy Freedom Power System (FPS-EX) Data Sheet; Published Jun. 2018.
http://www.altergy.com/wp-content/uploads/2017/09/Altergy_PSP_Data_sheet_6_ATP_web.pdf; Altergy Public Safety Platform Data Sheet; Published 2017.
http://www.altergy.com/wp-content/uploads/2017/09/Altergy_Nacelle_Data_sheet_ATP_web.pdf; Altergy Freedom Power System Nacelle Data Sheet; Published Feb. 2017.
http://www.altergy.com/wp-content/uploads/2016/08/Altergy_CorpBro_Web_singlePg.pdf; Altergy Corporate Brochure; Received Aug. 28, 2019.
http://www.altergy.com/wp-content/uploads/2017/09/Altergy_Cable_Data_sheet_ATP_web.pdf, Altergy Cable/Multiple-System Operators Data Sheet; Received Aug. 28, 2019.
https://www.hydrogenics.com/technology-resources/media-downloads-table/; Hydrogenics HyPM Rack Brochure; Published Mar. 2014.
https://www.hydrogenics.com/technology-resources/media-downloads-table/; Hydrogenics HyPM-XR Back-Up Power Fuel Cell Brochure; Published May 2016.
https://www.hydrogenics.com/hydrogen-products-solutions/fuel-cell-power-systems/; Hydrogenics HyPM-HD Power Modules Brochure; Published Feb. 2018.
https://www.intelligent-energy.com/uploads/product_docs/49087_IE_-_FCM_brochure_May_2018.pdf; Intelligent Energy 800 Series Fuel Cell Module Brochure; Published May 2018.
https://www.intelligent-energy.com/uploads/product_docs/Final_UAV_brochure_Sept_2018_web.pdf Intelligent Energy UAV Fuel Cell Power Module Brochure; Published Aug. 2018.
https://www.plugpower.com/wp-content/uploads/2016/03/2016_GenKey_Stationary020816.pdf; Plug Power GenKey for Stationary Power Brochure; Published Feb. 8, 2016.
https://www.plugpower.com/wp-content/uploads/2018/06/2018GenKeyBrochure_F1Digi-1.pdf; Plug Power GenKey for Material Handling Brochure; Published Jun. 2018.
https://www.plugpower.com/products/progen/fuel-cells-for-industrial-robotics/; Plug Power ProGen Fuel Cells for Industrial Robotics Webpage; Received Aug. 28, 2019.
https://www.arema.org/files/library/2014_Conference_Proceedings/Fuel_Cell_Technology_For_Backup_And_Supplemental_Power_Applications.pdf; Arema Fuel Cell Article; Jun. 13, 2014.
https://www.plugpower.com/wp-content/uploads/2015/05/Intelec2011_ReliOn_P081_IEEE.pdf; ReliOn Smart Energy Solutions Article; Joe Blanchard; Published Nov. 2011.
https://www.plugpower.com/wp-content/uploads/2015/05/ReliOnIntelec_2013Paper.pdf; ReliOn Superstorm Sandy: Fuel Cell Design Article; Spink and Saathoff; Published 2013.
https://www.plugpower.com/wp-content/uploads/2018/06/2018_GenFuelSpec_F1Digi.pdf; Plug Power GenFuel Hydrogen Solutions for Material Handling Applications; Published Jun. 2018.
https://www.plugpower.com/wp-content/uploads/2016/03/GenSureProductCatalogsm_012716.pdf; Plug Power GenSure Fuel Cell Systems Product Catalog; Published Mar. 2016.
https://www.plugpower.com/wp-content/uploads/2014/12/ColdStorageDigi_F_101716.pdf; Plug Power GenDrive Fuel Cells for Cold Chain Environments Brochure; Published Dec. 2014.
https://www.plugpower.com/wp-content/uploads/2016/07/Mfg_mktg_Final072216.pdf; Plug Power Fuel Cells for Manufacturing Facilities Brochure; Published Jul. 2016.
https://www.plugpower.com/wp-content/uploads/2019/04/ProGenSpec_Mobility_Digi0219.pdf; Plug Power ProGen Fuel Cell Power for E-Mobility Applications; Published Apr. 2019.
PCT International Search Report and Written Opinion for PCT/US2019/48543; Nov. 27, 2019.
https://energy.gov/sites/default/files/2015/11/f27/fcto_fuel_cells_fact_sheet.pdf; Fuel Cells Technologies Office Fuel Cells Fact Sheet; Nov. 2015.
https://www.energy.gov/eere/fuelcells/fuel-cell-systems; Office of Energy Efficiency & Renewable Energy "Fuel Cell Systems"; Department of Energy; Jan. 26, 2017.
https://www.cdc.gov/infectioncontrol/pdf/guidelines/disinfection-guidelines-H.pdf; CDC "Guideline for Disinfection and Sterilization in Healthcare Facilities" Rutala; Department of Health and Human Services; 2008.

SYSTEM TO STERILIZE A PHYSICAL SPACE

CROSS REFERENCE TO RELATED APPLICATIONS

The present application is a continuation of U.S. application Ser. No. 17/985,334 filed on Nov. 11, 2022, which is a continuation of U.S. application Ser. No. 17/493,429 filed on Oct. 4, 2021 now issued as U.S. Patent No. 11,502,314, which is a continuation of U.S. application Ser. No. 16/553,532 filed on Aug. 28, 2019 now issued as U.S. Pat. No. 11,139,488, which claims priority to U.S. Provisional Application No. 62/723,789 filed Aug. 28, 2018. Each of the aforementioned patent applications is herein incorporated by reference in their entirety.

STATEMENT REGARDING FEDERALLY SPONSORED RESEARCH OR DEVELOPMENT

Not applicable to this application.

BACKGROUND

Field

Example embodiments in general relate to a fuel-cell powered system for sterilizing a physical space to eradicate insects and microorganisms using heat.

Related Art

Any discussion of the related art throughout the specification should in no way be considered as an admission that such related art is widely known or forms part of common general knowledge in the field.

Hotel rooms, restaurants, and other physical spaces that are intended to be occupied from time to time by humans and sometimes animals can suffer from infestations of bed bugs, fruit flies, and other pests. The economic impact of bed bug infestations is significant, with 60% of respondents of a hotel industry survey stating that a report of bed bugs is the number one reason to leave a hotel.

In addition to bed bugs, fruit flies and other pests, hotel guests may be bothered by odors, pollen, and other allergens. In some instances, a hotel guest may be sickened or contract life-changing/life-threatening illnesses. For multiple reasons, a hotel owner, manager, or supervisor may wish to disinfect a specific hotel room or area.

Traditional methods for disinfection include the use of chemicals. This has proven to be partially effective, but the impact of a chemical treatment may be problematic. Typically, only one type of chemical may be used at a time, since mixing chemicals may be dangerous. Secondly, insects and microorganisms may develop a resistance to chemicals over time. Residuals from chemicals also may be hazardous to people and pets. Care is therefore required to carefully contain the chemicals used to only the area to which they are applied during treatment, and to remove all instances of the chemicals used after treatment is completed. Finally, the use of chemicals is not effective to treat instances of allergens, and may negatively contribute to problems of unwanted odors.

In some applications, heat has been used to treat bed bugs and other infestations. The use of heat to eliminate insects is superior in some ways to using chemicals, as insects cannot develop a resistance to heat in the way they can to chemical treatments. Further, heat treatments leave no residual chemicals behind to deal with. To date, heat used for disinfection purposes has been produced by large heaters located on the exterior premises of hotels. Internal combustion engines have been used to power the heaters and to provide air distribution to deliver the heat they produce to an area being treated. However, heaters and internal combustion engines are large and unsightly to hotel guests. In addition, the internal combustion engines produce large amounts of noise. The use of large external heaters powered by internal combustion engines to treat infestations may be effective, but may in turn discourage guests from staying in a hotel since the sights and sounds they produce in connection with the treatment process can create a negative image of the hotel.

Internal combustion engines likely cannot be used inside a structural enclosure, such as a hotel room or restaurant, where they may be less noticeable, as the emissions from the exhausts of internal combustion engines contain poisonous gasses and must be vented to the outside. Additionally, the noise generated by an internal combustion engine is too great for inside use. Accordingly, a system powered by an internal combustion engine to provide heat for disinfection requires the heat to be produced outside the location to be treated and to be directed from outside to the location to be treated by ducting. However, the ducting also may be problematic and is certainly likely to be noticed by guests, likely drawing unwanted attention to a location needing to be treated for infestation, and potentially reducing the guests' enjoyment of their hotel stay.

In other heat-based disinfection applications, electric heaters have been used to produce localized heating inside hotel rooms or other physical spaces needing heat treatment. However, the electrical requirements of such heaters far exceed the capabilities of typical hotel electrical systems, as each hotel room will typically have (at most) a single 15 A 120 VAC circuit, and such electrical heaters generally require four to eight 15 A 120 VAC circuits to generate the necessary heat. Two options are currently available for using such an electric heater inside a typical hotel room: 1) draw additional electrical power from additional rooms, taking the rooms out of service for potential hotel guests, or 2) have an electrical generator outside the building to provide the needed electricity. In each case, electrically connecting the heater inside the room or other physical space being treated to the additional electrical sources is likely to require the use of multiple electrical extension cords, which are expensive, waste power, and pose a potential tripping hazard. Further, in each case, the equipment for carrying out the sterilization method is non-discrete and is likely to be noticed by potential hotel guests, which may impact guests' enjoyment of the hotel and even cause them to choose a different hotel.

The system to sterilize a physical space embodying the present invention addresses the need to effectively disinfect or sterilize hotel rooms, restaurants, and other physical spaces that are intended to be occupied by people and perhaps animals, from infestations of bed bugs, fruit flies, cockroaches, and other insects. The system also addresses the need to provide treatment against various microorganisms, allergens, pollens, and unwanted odors. The system uses heat as an effective disinfectant agent while avoiding the problems of the known heat-based disinfection systems and methods. The system also provides additional options for treating against microorganisms, pollen and other allergens, and/or unwanted odors employing aerosols, ultraviolet light, and filtration. The system is self-contained, unobtrusive and near silent, allowing a hotel room or other physical space to be treated without drawing unwanted attention or bothering guests in adjacent rooms or spaces. The system may be used in any area affected by pests, allergens, odors, and/or microorganisms, including, but not limited to: hotels, motels, restaurants, hospitals, nursing homes, personal residences and homes, and businesses.

SUMMARY

An example embodiment is directed to a system to sterilize a physical space. The system includes a source of hydrogen and a hydrogen fuel cell that is adapted to receive the hydrogen and that is operable to use the hydrogen to generate electrical power. The source of hydrogen may comprise a tank or plurality of tanks containing compressed hydrogen, or a liquid feedstock and a reformer. The reformer is adapted to receive the liquid feedstock and is operable to produce hydrogen locally from the liquid feed stock for use by the fuel cell.

The system also includes an electrical system for that is adapted to receive the electrical power. The electrical system includes an electrical storage for holding stored electrical power and the electrical system is operable to store the electrical power generated by the fuel cell in the electrical storage. The electrical storage may comprise a battery. The electrical system also may include a power conditioner comprising electrical circuits operable to rectify and filter the electrical power. The electrical system is operable to provide the stored electrical power for use outside the electrical system. The stored electrical power is used to power other components of the system.

The system also includes a heater that is adapted to receive the stored electrical power and that is operable to produce heated air at a temperature sufficient to achieve a desired sterilization effect. The desired sterilization effect may comprise killing one or more insects and the temperature sufficient to achieve that desired sterilization effect may be a temperature in a range between about 120° F. and 140° F. The desired sterilization effect may comprise killing one or more microorganisms and the temperature sufficient to achieve that desired sterilization effect may be a temperature that exceeds about 100° F.

The system further includes an air distributor that is adapted to receive the stored electrical power and that is operable to distribute the heated air into a physical space to be disinfected or sterilized. The air distributor may comprise a fan.

The system includes a portable housing, which may comprise a mobile cart with wheels. The source of hydrogen, the hydrogen fuel cell, the electrical system, the heater, and the air distributor are mounted to the portable housing. The portable housing may be moved into and contained within a room or other structure comprising a physical space to be disinfected or sterilized, and the system may be utilized to disinfect or sterilize the physical space.

The portable housing may include an electrical connection that is adapted to receive the stored electrical power from the electrical system and to provide the stored electrical power for use outside the portable housing. The stored electrical power provided by the electrical connection may be used to power peripherals and other components of the system.

The system may include a peripheral that is adapted to be coupled to the electrical connection and to receive the stored electrical power. The peripheral may be located in the physical space and may comprise a fan, a sensor, or a light source.

The system may include a UV light source adapted to be coupled to the electrical connection and to receive the stored electrical power. The UV light source is operable to provide UV light for treating against microorganisms. The UV light source may be located in the physical space to treat against microorganisms in the physical space.

The system may include a control unit. The control unit is mounted to the portable housing and is adapted to receive the stored electrical power from the electrical system. The control unit is in communication with the fuel cell, the electrical system, the heater, and the air distributor. The control unit is configured to monitor the operational status of the fuel cell, the electrical system, the heater, and the air distributor, control the operation of the fuel cell, the electrical system, the heater, and the air distributor, and log data about the operational status of the fuel cell, the electrical system, the heater, and the air distributor.

The control unit may include a control panel comprised of a display and a plurality of information entry keys. The control unit is configured to display the data about the operational status on the display, receive information for controlling the operation of the fuel cell, the electrical system, the heater, and the air distributor via the information entry keys, and control the operation of the fuel cell, the electrical system, the heater, and the air distributor based on the information received.

The system also may include an aerosol dispenser. The aerosol dispenser may be mounted to the portable housing, is adapted to receive the stored electrical power, and is operable to dispense an aerosol into the physical space for disinfection and deodorization.

The system may further include a filter. The filter is mounted to the portable housing, is adapted to receive the heated air from the air distributor, and is operable to remove particulates from the heated air.

There has thus been outlined, rather broadly, some of the embodiments of the system to sterilize a physical space in order that the detailed description thereof may be better understood, and in order that the present contribution to the art may be better appreciated. There are additional embodiments of the system to sterilize a physical space that will be described hereinafter and that will form the subject matter of the claims appended hereto. In this respect, before explaining at least one embodiment of the system to sterilize a physical space in detail, it is to be understood that the system to sterilize a physical space is not limited in its application to the details of construction or to the arrangements of the components set forth in the following description or illustrated in the drawings. The system to sterilize a physical space is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION

Figure 1:
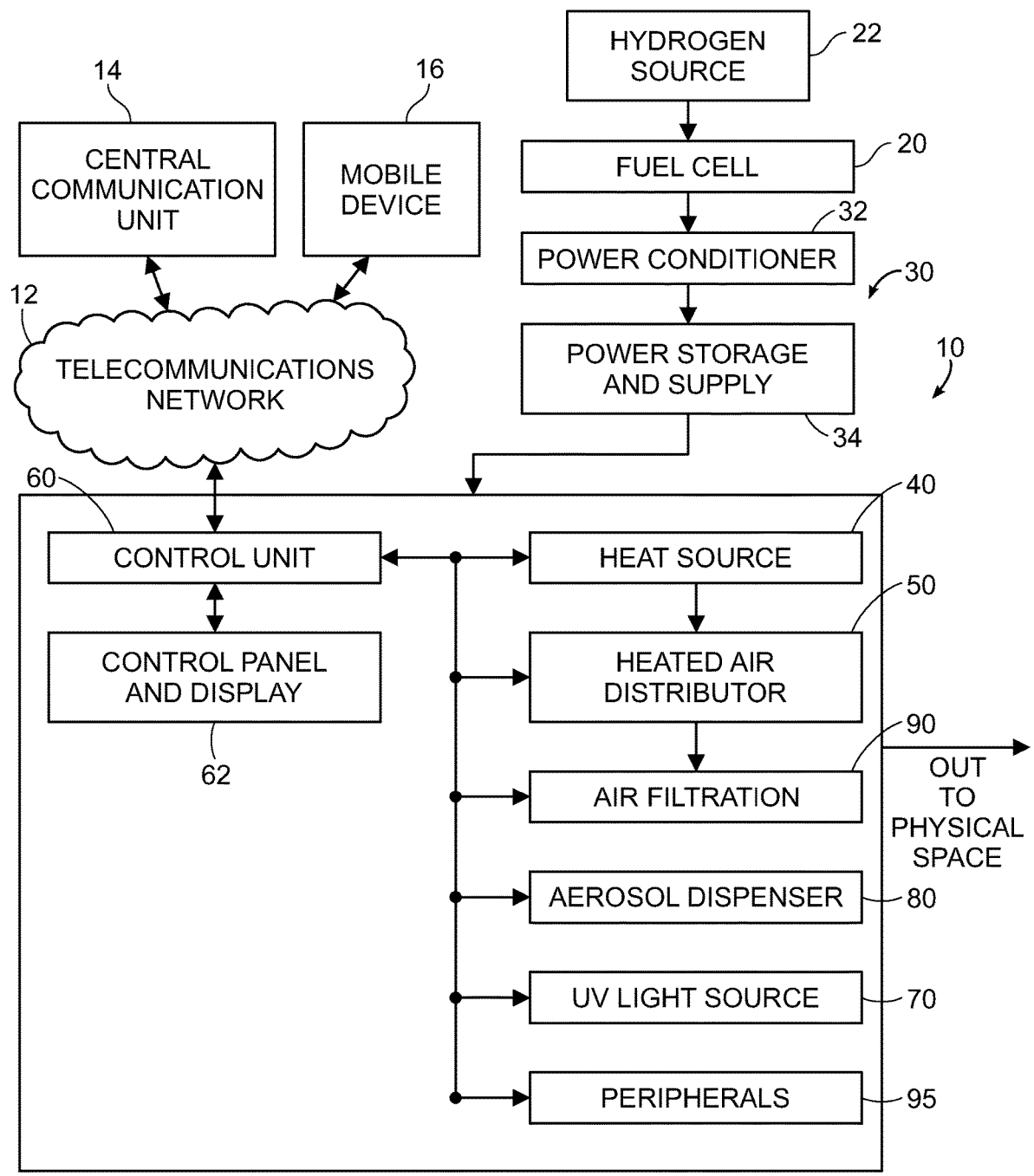
FIG. 1 is a block diagram illustrating the functional relationship between components of a system to sterilize a physical space in accordance with an example embodiment.
Figure 2:
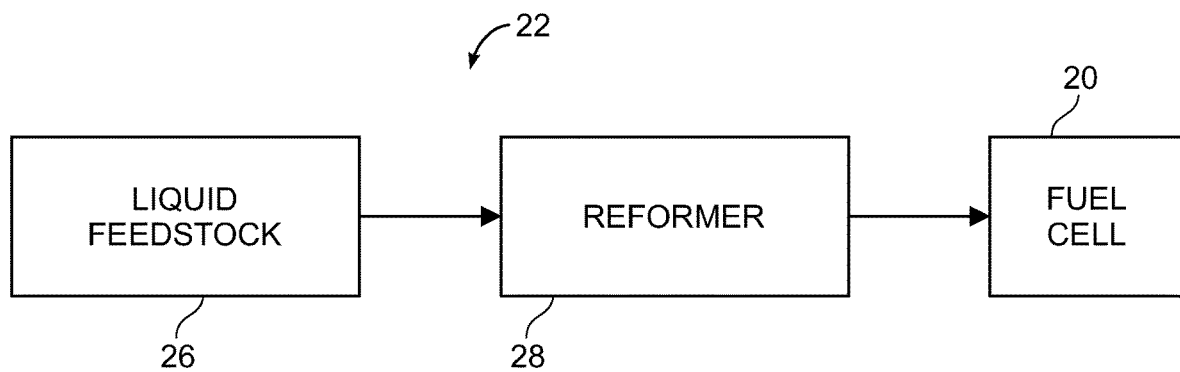
FIG. 2 is a block diagram illustrating the components of one hydrogen source for a fuel cell of a system to sterilize a physical space in accordance with an example embodiment.

Example embodiments of a system to sterilize a physical space 10 are described below with reference to FIGS. 1-7.

A. Overview

Example embodiments of a system to sterilize a physical space 10 generally include a source of hydrogen 22 and a hydrogen fuel cell 20 that uses the hydrogen to generate electrical power. The hydrogen source 22 may comprise a tank 24 or a plurality of tanks 24 connected by a manifold system containing compressed hydrogen, or a liquid feedstock 26 and a reformer 28 that uses the liquid feed stock 26 to produce hydrogen locally.

The system 10 also includes an electrical system 30 that includes a battery or bank of batteries 36 for storing the electrical power produced by the hydrogen fuel cell 20. The electrical system 30 may include a power conditioner 32 including electrical circuits to rectify and filter the electrical power from the hydrogen fuel cell 20 before it is stored. The stored electrical power is used to power the other components of the system.

The system 10 also includes a heater 40. The heater 40 is powered by the stored electrical power and is operated to produce heated air in a temperature range that is sufficient to produce a disinfectant or sterilization effect in a physical space, such as a hotel room, restaurant, or other confined space. The disinfectant or sterilization effect includes killing insects and microorganisms.

The system 10 further includes an air distributor 50, which may include one or more fans 52. The air distributor 50 is powered by the stored electrical power and operates to distribute the air heated by the heater 40 into the physical space to be disinfected or sterilized.

The system may further include a filter 90 such as a HEPA filter. The filter 90 removes particulates from the heated air as it is distributed into the physical space being disinfected or sterilized.

The system 10 includes a control unit 60. The control unit 60 is in communication with the system components, including the source of hydrogen 22, the fuel cell 20, the electrical system 30, the heater 40, and the air distributor 50. The control unit 60 may also be in communication with a UV light source 70, aerosol dispenser 80, and other peripherals 95, if used.

The control unit 60 is configured to monitor and to collect and log data about the operational status of the various system components. The control unit 60 is also configured to control the operation of the various system components.

The control unit 60 includes a control panel 62 having a display 64 and a plurality of information entry keys 66. The control unit 60 and the control panel 62 are powered by the stored electrical power. The control unit 60 displays the data about the operational status of the system components on the display 64, and receives information for controlling the operation of the system via the information entry keys 66.

The system 10 includes a portable housing 100 to which all of the components of the system are mounted and/or within which all of the components of the system are disposed in whole or in part. The portable housing 100 preferably comprises a mobile cart 101 with wheels 102, thus enabling the system to be self-contained and easily moved into and contained within a physical space to be disinfected or sterilized.

The mobile cart 101 includes an electrical connection 39 that is exposed outside of the mobile cart 101 and that provides access to the stored electrical power for use by peripherals and other components of the system outside the portable housing 100 in the physical space being disinfected or sterilized.

One or more UV light sources 70 may be used with the system and can be connected to the electrical connection 39 and be powered by the stored electrical power. The UV light sources 70 can be positioned at various locations within the physical space to irradiate the physical space with UV light to kill microorganisms that may be resistant to eradication from heat alone.

One or more aerosol dispensers 80 can be used with the system 10 and be connected to the electrical connection 39 and be powered by the stored electrical power. The aerosol dispenser 80 dispenses an aerosol into the physical space to provide additional disinfection and deodorization effects.

Other peripherals 95 can be connected to the electrical connection 39 and be powered by the stored electrical power. Other peripherals 95 can include one or more remote fans, one or more temperature or other sensors, and one or more light sources.

B. Exemplary Telecommunications Networks

The system to sterilize a physical space 10 may be utilized with and upon any telecommunications network 12 capable of transmitting data including voice data and other types of electronic data. Examples of suitable telecommunications networks for the system to sterilize a physical space include but are not limited to global computer networks (e.g. Internet), wireless networks, cellular networks, satellite communications networks, cable communication networks (via a cable modem), microwave communications network, local area networks (LAN), wide area networks (WAN), campus area networks (CAN), metropolitan-area networks (MAN), and home area networks (HAN). The system to sterilize a physical space 10 may communicate via a single telecommunications network 12 or multiple telecommunications networks concurrently. Various protocols may be utilized by the electronic devices for communications such as but not limited to HTTP, SMTP, FTP and WAP (wireless Application Protocol). The system to sterilize a physical space 10 may be implemented upon various wireless networks such as but not limited to 3G, 4G, LTE, CDPD, CDMA, GSM, PDC, PHS, TDMA, FLEX, REFLEX, IDEN, TETRA, DECT, DATATAC, and MOBITEX. The system to sterilize a physical space 10 may also be utilized with online services and internet service providers.

The Internet is an exemplary telecommunications network for the system to sterilize a physical space 10. The Internet is comprised of a global computer network having a plurality of computer systems around the world that are in communication with one another. Via the Internet, the computer systems are able to transmit various types of data between one another. The communications between the computer systems may be accomplished via various methods such as but not limited to wireless, Ethernet, cable, direct connection, telephone lines, and satellite.

C. Central Communication Unit

The central communication unit 14 may be comprised of any central communication site where communications are preferably established with. The central communication units 14 may be comprised of a server computer, cloud based computer, virtual computer, home computer or other computer system capable of receiving and transmitting data via IP networks and the telecommunication networks. As can be appreciated, a modem or other communication device may be required between each of the central communication units 14 and the corresponding telecommunication networks 12. The central communication unit 14 may be comprised of any electronic system capable of receiving and transmitting information (e.g. voice data, computer data, etc.).

D. Mobile Device

The mobile device 16 may be comprised of any type of computer for practicing the various aspects of the system to sterilize a physical space 10. For example, the mobile device 16 can be a personal computer (e.g. APPLE® based computer, an IBM based computer, or compatible thereof) or tablet computer (e.g. IPAD®). The mobile device 16 may also be comprised of various other electronic devices capable of sending and receiving electronic data including but not limited to smartphones, mobile phones, telephones, personal digital assistants (PDAs), mobile electronic devices, handheld wireless devices, two-way radios, smart phones, communicators, video viewing units, television units, television receivers, cable television receivers, pagers, communication devices, and digital satellite receiver units.

The mobile device 16 may be comprised of any conventional computer. A conventional computer preferably includes a display screen (or monitor), a printer, a hard disk drive, a network interface, and a keyboard. A conventional computer also includes a microprocessor, a memory bus, random access memory (RAM), read only memory (ROM), a peripheral bus, and a keyboard controller. The microprocessor is a general-purpose digital processor that controls the operation of the computer. The microprocessor can be a single-chip processor or implemented with multiple components. Using instructions retrieved from memory, the microprocessor controls the reception and manipulations of input data and the output and display of data on output devices. The memory bus is utilized by the microprocessor to access the RAM and the ROM. RAM is used by microprocessor as a general storage area and as scratch-pad memory, and can also be used to store input data and processed data. ROM can be used to store instructions or program code followed by microprocessor as well as other data. A peripheral bus is used to access the input, output and storage devices used by the computer. In the described embodiments, these devices include a display screen, a printer device, a hard disk drive, and a network interface. A keyboard controller is used to receive input from the keyboard and send decoded symbols for each pressed key to microprocessor over bus. The keyboard is used by a user to input commands and other instructions to the computer system. Other types of user input devices can also be used in conjunction with the system to sterilize a physical space. For example, pointing devices such as a computer mouse, a track ball, a stylus, or a tablet to manipulate a pointer on a screen of the computer system. The display screen is an output device that displays images of data provided by the microprocessor via the peripheral bus or provided by other components in the computer. The printer device when operating as a printer provides an image on a sheet of paper or a similar surface. The hard disk drive can be utilized to store various types of data. The microprocessor, together with an operating system, operates to execute computer code and produce and use data. The computer code and data may reside on RAM, ROM, or hard disk drive. The computer code and data can also reside on a removable program medium and loaded or installed onto computer system when needed. Removable program mediums include, for example, CD-ROM, PC-CARD, USB drives, floppy disk and magnetic tape. The network interface circuit is utilized to send and receive data over a network connected to other computer systems. An interface card or similar device and appropriate software implemented by microprocessor can be utilized to connect the computer system to an existing network and transfer data according to standard protocols.

E. Hydrogen Fuel Cell

The main power source of the system to sterilize a physical space 10 is a hydrogen fuel cell 20. While the description herein refers to the hydrogen fuel cell 20 in the singular for ease of description, those skilled in the art will appreciate that the hydrogen fuel cell 20 may, and likely will, comprise a plurality of hydrogen fuel cells in a hydrogen fuel cell system. Reference to the hydrogen fuel cell 20 in the singular is thus intended to encompass and not to exclude a plurality of hydrogen fuel cells and/or a hydrogen fuel cell system.

The use of a hydrogen fuel cell 20 as the main power source for the system to sterilize a physical space 10 enables the system to be mobile, self-contained, and to operate without requiring electrical connection to an outside source of electrical power, such as the AC electrical system of a hotel, restaurant or other facility. The system to sterilize a physical space 10 can thus be completely contained and used inside a hotel room or other physical space to disinfect or sterilize the physical space without running a generator, or connecting multiple electrical cables from electrical outlets in the physical space, and perhaps adjoining spaces, to the system. The system to sterilize a physical space 10 is thus able to operate unobtrusively, unseen, and without attracting undesired attention by persons outside a physical space to an on-going disinfection or sterilization process.

The hydrogen fuel cell 20 is adapted to receive hydrogen from a source of hydrogen 22. The hydrogen fuel cell 20 is operable to use the hydrogen provided by the source of hydrogen 22 for generating electrical power. The electrical power generated by the hydrogen fuel cell 20 is used to power the other components of the system to sterilize a physical space 10. These include, but are not limited to, a heat source 40 comprising a heater or plurality of heaters, an air distributor 50 comprising a fan 52 or a plurality of fans, a control unit 60 and embedded electronics, and various peripherals, including but not limited to one or more ultraviolet light (UV) sources 70, one or more aerosol dispensers 80, a filter 90, and other peripherals 95, all of which are further described below.

The hydrogen fuel cell 20 is electrically coupled to the electrical system 30 of the system to sterilize a physical space 10, more particularly to the power conditioner 32 and electrical storage 34 of the electrical system 30, and still more particularly to the battery 36 of the electrical storage 34 of the electrical system 30. The hydrogen fuel cell 20 is electrically coupled via the electrical system 30 to the other components of the system to sterilize a physical space 10, including but not limited to the heat source 40, air distributor 50, including fan 52, control unit 60, and various peripherals, ultraviolet light (UV) sources 70, aerosol dispensers 80, filter 90, and other peripherals 95.

Fuel cell power systems have been in existence for nearly two hundred years, with their commercial viability increasing in the recent past. The process used by fuel cell power systems is an electrochemical process, unlike the combustion process used in internal combustion engines. The hydrogen fuel cell 20 is near silent while generating electrical power, and has an energy efficiency (defined as energy of the electricity produced compared to the energy content of the hydrogen consumed by the fuel cell) of approximately 50%. This is a higher value than the efficiency realized by internal combustion engines (defined as the mechanical energy available at the output of the engine compared to the energy content of the fuel consumed). The system to sterilize a physical space 10 is thus able to operate efficiently, unobtrusively and without attracting undesired attention to an on-going disinfection or sterilization process.

The hydrogen fuel cell 20 is coupled to the source of hydrogen 22 by suitable plumbing components. The source of hydrogen 22 supplies hydrogen to the hydrogen fuel cell 20 via the plumbing components and the hydrogen fuel cell 20 chemically combines the hydrogen with atmospheric oxygen to directly produce electricity and radiated heat. The hydrogen fuel cell 20 produces as an exhaust product liquid water. The water may be used for any purpose (with appropriate treatment to eliminate any contaminants that may be introduced after the fuel cell system), or may be discharged into a gray water/black water drain or collection system without any harm. Unlike internal combustion engines, the exhaust of the hydrogen fuel cell 20 does not contain poisonous gasses.

The hydrogen fuel cell 20 is connected to and is in in communication with the control unit 60 of the system to sterilize a physical space 10 via one or more suitable wired or wireless network or direct connections. As further described below, the hydrogen fuel cell 20 communicates operational status information to the control unit 60. The hydrogen fuel cell 20 also receives and responds to control commands from the control unit 60.

It is noted that the electrical power generated by the hydrogen fuel cell 20 could be used to directly power the various components and peripherals of the system. However, for a variety of reasons, it is preferred that the electrical power generated by the hydrogen fuel cell 20 first be provided to and processed by an electrical system 30 before being provided to power the various components and peripherals.

F. Hydrogen Source

The source of hydrogen 22 provides the hydrogen that the hydrogen fuel cell 20 uses to generate electrical power for the system to sterilize a physical space 10. The source of hydrogen 22 may comprise stored compressed hydrogen. The compressed hydrogen may be stored locally in a tank 24 or a plurality of tanks 24 connected by a manifold system. However, there may be instances where the storage of compressed hydrogen locally on a site or in a room or other physical space to be disinfected or sterilized is undesired.

It is therefore preferred that the source of hydrogen 22 comprise a liquid feedstock 26 and a reformer 28. The reformer 28 is adapted to receive the liquid feedstock 26, and the reformer 28 is operable to produce hydrogen locally from the liquid feed stock 26. The liquid feedstock may be stored in a tank or in a plurality of tanks, depending on the volume of hydrogen to be produced. The reformer 28 may be coupled to the liquid feedstock 26 by suitable plumbing components. The liquid feedstock 26 and reformer 28 should be selected to be capable of providing sufficient hydrogen for the hydrogen fuel cell 20 to produce sufficient electrical power to power all of the components and peripherals of the system to sterilize a physical space 10, and for the system to produce a desired sterilization effect in a physical space being disinfected or sterilized.

The reformer 28 preferably includes suitable filters and the like to purify the hydrogen. The hydrogen produced by the reformer 28 may be stored in tank 24 or in a plurality of tanks 24 connected by a manifold system for use by the hydrogen fuel cell.

In a preferred embodiment, the reformer 28 uses a combination of methanol and deionized water to create the hydrogen, using an electrical heater as a heating source to "crack" the methanol/deionized water mixture to create pure hydrogen. Electrical power for energizing the electrical heater may be supplied by electrically connecting the heater to a standard electrical connector of a standard AC circuit of the premises having a room or other physical space to be disinfected. Alternatively, and preferably, the reformer is electrically coupled to the electrical system 30 of the system to sterilize a physical space 10, and the electrical power for the heater can be supplied from the stored electrical power in the electrical storage 34 of the electrical system 30, and more particularly the batteries 36, all of which are further described herein.

In this embodiment, there is no potential for spark or a hazardous environment. The combination of methanol and deionized water is not a biohazard if spilled, since the half-life of the feedstock is approximately ten days. Furthermore, if the feedstock of methanol and deionized water is chilled below fifty degrees Fahrenheit ("F."), the feedstock is not combustible since the vapor pressure is too low to ignite. A refrigerant-based cooler may be used for this purpose if desired.

In the event the hydrogen produced by the reformer 28 exceeds a predetermined pressure limit or it is otherwise desired or necessary to purge hydrogen from the system, a hydrogen purge line and valve 29 may be provided and connected to the system using suitable plumbing components.

The source of hydrogen 22 is connected to and is in in communication with the control unit 60 of the system to sterilize a physical space 10 via one or more suitable wired or wireless network or direct connections. As further described below, the source of hydrogen 22, and in particular the reformer 28, can communicate operational status information to the control unit 60. The source of hydrogen 22, and in particular the reformer 28, can also receive and respond to control commands from the control unit 60.

G. Electrical System

The electrical system 30 of the system to sterilize a physical space 10 is adapted to receive the electrical power generated by the hydrogen fuel cell 20. The electrical system 30 comprises an electrical storage 34 for holding stored electrical power, and the electrical system 30 is operable to store the electrical power generated by the hydrogen fuel cell 20 in the electrical storage 34. The electrical system 30 is then operable to provide the stored electrical power from the electrical storage 34 for use outside the electrical system 30 to power the other components and peripherals of the system to sterilize a physical space 10.

The electrical system 30 also comprises a power conditioner 32. The power conditioner 32 receives and processes the electrical power generated by the hydrogen fuel cell 20 into a more suitable form for storing and for powering the various components and peripherals of the system to sterilize a physical space 10. The power conditioner 32 thus comprises electrical circuits operable to rectify and filter the electrical power generated by the hydrogen fuel cell 20 before storing it in the electrical storage 34 and before the stored power is supplied to power the various components and peripherals of the system to sterilize a physical space 10. The power conditioner 32 may comprise one or more inverters 38 for these purposes, including converting electrical power between DC and AC forms as required by the electrical storage system 34 and the various components and peripherals of the system for sterilizing a physical space 10.

The electrical system 30, and more particularly the power conditioner 32, is electrically coupled to the hydrogen fuel cell 20 by suitable electrical wiring and components. The power conditioner 32 is further electrically coupled to the electrical storage 34 by suitable electrical wiring and components.

The electrical system 30, and more particularly the electrical storage 34, is also electrically coupled by suitable electrical wiring and components to the other components and peripherals of the system for sterilizing a physical space 10, including but not limited to heat source 40, air distributor 50, control unit 60, ultraviolet light (UV) sources 70, aerosol dispensers 80, filter 90, and other peripherals 95. The electrical storage 34 supplies stored electrical power to the various components and peripherals of the system to sterilize a physical space 10 described herein to power the various components and peripherals.

The electrical storage 34 preferably comprises one or more batteries 36. If multiple batteries 36 are employed, they are preferably wired together in one or more banks. Each bank may be wired with the batteries 34 in series or in parallel, depending on the number of batteries 34, the electrical specifications of the batteries 34, and the electrical voltage, amperage, and power requirements of the various components and peripherals of the system to sterilize a physical space 10. Separate battery banks may be wired in different ways as desired or needed.

The battery or batteries 36 of the electrical storage 34 supply the stored electrical power to the various components and peripherals of the system to sterilize a physical space 10 described herein to power the various components and peripherals. The batteries also supply stored electrical power to power any other outside peripherals that a user of the system to sterilize a physical space 10 might desire to electrically connect to and be powered by the system. Accordingly, the batteries 36 are electrically connected by suitable electrical wiring and components to each of the components and peripherals of the system to sterilize a physical space 10 described herein, including but not limited to heat source 40, air distributor 50, control unit 60, ultraviolet light (UV) sources 70, aerosol dispensers 80, and filter 90. The battery or batteries 36 are also electrically connected by suitable electrical wiring and components to one or more electrical connections 39 to which peripherals of the system, including other outside peripherals 95 may be electrically connected as described further below.

The inverters 38 also may provide electrical connections 39 directly for the same purpose if desired. The inverters 38 also are operable to convert the stored electrical power from the electrical storage 34 from DC to AC before the stored electrical power is supplied to the electrical connections 39 and directly to those components and peripherals requiring AC power to operate.

The electrical system 30 is connected to and is in in communication with the control unit 60 of the system to sterilize a physical space 10 via one or more suitable wired or wireless network or direct connections. As further described below, the electrical system 30 communicates operational status information to the control unit 60. The electrical system 30 also receives and responds to control commands from the control unit 60.

If desired, the system to sterilize a physical space 10 may also include a battery charger 35 adapted to be electrically connected to and powered by a source of power other than the hydrogen fuel cell 20. If included, an electrical input of the battery charger 35 is preferably adapted to be connected to a standard power connector of a standard AC electrical circuit. The battery charger 35 may be connected to a power connector of the premises containing a room or other physical space to be disinfected or sterilized or to a power connector of another site or location before the system to sterilize a physical space 10 is transported to the premises having the physical space to be disinfected or sterilized. The electrical input of the battery charger 35 may be connected to the standard power connector by a short length of standard electrical wire or cable. An electrical output of the battery charger 35 may be electrically connected to the electrical storage 34, and more particularly to the battery or batteries 36 and provide a source of charging power to charge the batteries 36.

The battery charger 35 may be energized to initially charge the batteries 36 with an amount of stored electrical power sufficient to power at least some of the components of the system to sterilize a physical space 10, such as the control unit 60 and the reformer 28. The control unit 60 may then control the reformer 28 to produce hydrogen for the hydrogen fuel cell 20, the fuel cell 20 to generate electrical power, and the electrical system 30 to store the electrical power in the electrical storage 34, and more particularly the batteries 36, until the batteries 36 are fully charged. The battery charger 35 also may be energized to provide assistance to the hydrogen fuel cell 20 and the electrical system 30 to charge or maintain the charge of the batteries 36 with stored electrical power.

The system to sterilize a physical space 10 may also include an electrical disconnect switch 37. The electrical disconnect switch 37 is operable to disconnect the electrical power generated by the hydrogen fuel cell 20 and the stored power supplied by the electrical system 30, more particularly the electrical storage 34, from the components and peripherals of the system to sterilize a physical space 10. Accordingly, the electrical disconnect switch 37 is electrically connected between the hydrogen fuel cell 20 and the electrical system 30, more particularly the electrical storage 34, on one hand and the various components, peripherals and electrical connections of the system on the other hand.

The electrical disconnect switch 37 may comprise a standard manual rotary electrical switch with open and closed positions. However, if desired, the electrical disconnect switch 37 may comprise another type of switch, such as a toggle switch. The electrical disconnect switch 37 also may comprise a multi-position switch, for example one that is operable in a first position to connect and disconnect an electrical output of the hydrogen fuel cell 20 to the components and peripherals, and that is operable in a second position to connect and disconnect the terminals of the electrical storage 34, or more particularly the batteries 36, to the components and peripherals. In still another position, the electrical disconnect switch 37 could be operable to connect and disconnect both the hydrogen fuel cell 20 and the electrical storage 34 to the components and peripherals.

H. Heater

The heater 40 of the system to sterilize a physical space 10 is electrically coupled to the electrical system 30, more particularly to the power conditioner 32 and electrical storage 34 of the electrical system 30, and still more particularly to the battery 36 of the electrical storage 34 of the electrical system 30. The heater 40 is electrically coupled via the electrical system 30 to the hydrogen fuel cell 20. Although a single heater 40 is referred to for ease of description herein, those skilled in the art will appreciate that a plurality of heaters may be included in the system and the reference to heater 40 in the singular is meant to encompass and not to exclude that variation.

The heater 40 is adapted to receive and be powered by the stored electrical power from the electrical storage 34 of the electrical system 30, and more particularly the batteries 36. The heater 40 may be DC or AC powered consistent with the description of the electrical system 30 above. Although the use of an electrical heater is preferred, the heater 40 may comprise another type of heater, provided it is capable of producing heated air at a temperature sufficient to achieve a desired sterilization effect, as described below.

The heater 40 is operable to produce heated air at a temperature sufficient to achieve a desired sterilization effect. The desired sterilization effect may comprise killing one or more insects in the physical space being disinfected or sterilized. It has been found that prolonged exposure to temperatures between about 120° F. and 140° F. is effective to kill insects, from larval stages to mature adults. Thus, the temperature of the heated air sufficient to achieve the desired sterilization effect of killing one or more insects in the physical space is a temperature between about 120° F. and 140° F.

The desired sterilization effect may comprise killing one or more microorganisms in the physical space being disinfected or sterilized. It has been found that continuous exposure to temperatures exceeding about 100° F. is effective to kill microorganisms such as bacteria and viruses. Thus, the temperature of the heated air sufficient to achieve the desired sterilization effect of killing one or more microorganisms in the physical space is a temperature that exceeds about 100° F.

The heater 40 may be operated for a period of time necessary to elevate the temperature of the air in a room or other physical space being disinfected or sterilized to the temperature sufficient to achieve the desired sterilization effect. The air distributor 50 of the system to sterilize a physical space 10, which is described further below, operates to recirculate air between the physical space and the heater 40 so that the temperature of the air in the physical space is initially elevated to the desired temperature, and then maintained at that temperature for a sufficient period of time to achieve the desired sterilization effect as described above. This period of time is referred to as the dwell time.

The heater 40 is connected to and is in in communication with the control unit 60 of the system to sterilize a physical space 10 via one or more suitable wired or wireless network or direct connections. As further described below, the heater 40 communicates operational status information to the control unit 60. The heater 40 also receives and responds to control commands from the control unit 60, including turning on and off, and setting the temperature at which to heat the air.

The heater 40 can be controlled by the control unit 60 to turn on and off and/or adjust the temperature to which the heater 40 is heating the air based on air temperature readings provided by sensors in the physical space. This enables the system 10 to operate automatically to elevate the temperature of the air in a physical space to a temperature sufficient to achieve a desired sterilization effect, to maintain the temperature for a desired dwell time, and to shut down and allow the air temperature in the physical space to return to normal.

By employing heated air to achieve the desired sterilization effect, the system to sterilize a physical space 10 provides major benefits over conventional chemical disinfection and sterilization systems and methods. For one thing, there are no residual chemical effects to be dealt with following completion of the disinfection or sterilization process when heat is used. For another, microorganisms, such as bacteria and viruses, and insects cannot develop resistance to heat like they can to chemicals.

I. Air Distributor

The air distributor 50 of the system to sterilize a physical space 10 is electrically coupled to the electrical system 30, more particularly to the power conditioner 32 and electrical storage 34 of the electrical system 30, and still more particularly to the battery 36 of the electrical storage 34 of the electrical system 30. The air distributor 50 is electrically coupled via the electrical system 30 to the hydrogen fuel cell 20. Although a single air distributor 50 is referred to for ease of description herein, those skilled in the art will appreciate that a plurality of air distributors 50 may be included in the system and the reference to air distributor 50 in the singular is meant to encompass and not to exclude that variation.

The air distributor 50 is adapted to receive and be powered by the stored electrical power from the electrical storage 34 of the electrical system 30, and more particularly the batteries 36. The air distributor 50 may be DC or AC powered consistent with the description of the electrical system 30 above.

The air distributor 50 is operable to distribute the heated air produced by the heater 40 into and throughout a room or other physical space being disinfected or sterilized. The air distributor 50 also is operable to recirculate the air between the physical space and the heater 40 in order to elevate the temperature in the physical space and then maintain it at the elevated temperature during a dwell time as described above.

The air distributor 50 preferably comprises one or more electronically-controlled fans 52. The fan(s) do not need to be high speed fans or to produce high static pressure for the system to sterilize a physical space 10 to be effective. One criteria of the fan design is low noise. Low fan noise is a desirable characteristic in that it enables the system to sterilize a physical space 10 to be operated in a hotel room or other physical space to disinfect or sterilize the space without bothering guests in adjacent rooms or physical spaces or calling unwanted attention to the fact a disinfection or sterilization process is being carried out next door.

The air distributor 50 may distribute the heated air into the room or other physical space directly or via ducting. Unlike the ducting used to deliver heated air from external heaters to a room being disinfected in conventional disinfection systems described herein, the ducting used can be entirely contained within the physical space being disinfected or sterilized. Thus, it is not seen by hotel guests or others outside the physical space being treated, and does not draw unwanted attention to the fact that a disinfection or sterilization treatment is underway.

The air distributor 50 is connected to and is in communication with the control unit 60 via one or more suitable wired or wireless network or direct connections. As further described below, the air distributor 50 communicates operational status information to the control unit 60. The air distributor 50 also receives and responds to control commands from the control unit 60, including turning on and off, and setting the speed of the fan 52.

While a manually operable fan 52 may be used, an electronically-controlled fan 52 is preferred because an electronically-controlled fan 52 can be controlled by the control unit 60 to turn the fan 52 on and off and/or adjust its speed based on air temperature readings provided by sensors in the physical space. This enables the system to operate automatically to elevate the temperature of the air in a physical space to a temperature sufficient to achieve a desired sterilization effect, to maintain the temperature for a desired dwell time, and to shut down and allow the air temperature in the physical space to return to normal.

The system to sterilize a physical space 10 may include a filter 90. The filter 90 is adapted to receive the heated air from the air distributor 50 and is operable to remove particulates from the heated air. The filter 90 thus functions to remove particulates from the heated air before it is distributed into the physical space being disinfected or sterilized by the air distributor 50. As the air distributor 50 operates to recirculate air between the physical space and the heater 40, a continuous flow of the air passes through the filter 90 so that particulates are continuously removed.

The filter 90 is referred to in the singular herein for ease of description. However, those skilled in the art will appreciate that a plurality of filters 90 may be included in the system and the reference to filter 90 in the singular is meant to encompass and not to exclude that variation. To the extent the filter comprises electronic filter components, such as electrostatic components, they may be DC or AC powered consistent with the description of the electrical system 30 above.

The filter 90 preferably comprises a high efficiency particulate air (HEPA) filtration system to eliminate airborne particles, pollens, and/or allergens. Filter elements may be replaced and/or installed for the treatment of particular airborne particles, as desired, and may be a replaceable item between disinfection and sterilization treatments.

The filter 90 may be connected to and be in communication with the control unit 60 of the system to sterilize a physical space 10 via one or more suitable wired or wireless network or direct connections. As further described below, the filter 90 may communicate operational status information to the control unit 60. To the extent the filter 90 comprises electronic filter components, it may also receive and respond to control commands from the control unit 60, for example to energize and de-energize the components.

J. Control Unit

The control unit 60 of the system to sterilize a physical space 10 may be comprised of any type of computer for practicing the various aspects of the system for sterilizing a physical space. For example, the control unit 60 can be a personal computer (e.g. APPLE® based computer, an IBM based computer, or compatible thereof) or tablet computer (e.g. IPAD®). The control unit 60 may also be comprised of various other electronic devices capable of sending and receiving electronic data including but not limited to smartphones, mobile phones, telephones, personal digital assistants (PDAs), mobile electronic devices, handheld wireless devices, two-way radios, smart phones, communicators, video viewing units, television units, television receivers, cable television receivers, pagers, communication devices, and digital satellite receiver units. Further, the control unit 60 may comprise one or more processors, microcontrollers, digital, analog, or mixed circuits, software, firmware, and internal or external configuration elements, such as programming, code, macros, and the like. Still further, the control unit 60 may comprise data storage such as a magnetic disk or tape, optical media, or a solid-state storage device.

The control unit 60 is electrically coupled to the electrical system 30, more particularly to the power conditioner 32 and electrical storage 34 of the electrical system 30, and still more particularly to the battery 36 of the electrical storage 34 of the electrical system 30. The control unit 60 is electrically coupled via the electrical system 30 to the hydrogen fuel cell 20. The control unit 60 is adapted to receive and to be powered by the stored electrical power from the electrical storage 34 of the electrical system 30, and more particularly the batteries 36.

The control unit 60 is in communication via suitable wired or wireless network or direct connections with the fuel cell 20, the source of hydrogen 22, the electrical system 30, and more particularly the power conditioner, 32, electrical storage 34, and batteries 36 of the electrical system, the heater 40, the air distributor 50, the filter 90, and various sensors and other peripherals described further below.

The control unit 60 is configured to monitor the operational status of the components and peripherals of the system to sterilize a physical space 10, including the fuel cell 20, the source of hydrogen 22, the electrical system 30 and its components, the heater 40, and the air distributor 50 and its components. The control unit 60 may obtain information about the operational status of the various components upon request, or may receive periodic communications from the components.

For example, the control unit 60 may monitor the volume of hydrogen generated and/or stored by the source of hydrogen 22, the rate and volume of the hydrogen being used by the fuel cell 20, and the electrical power being generated by the fuel cell 20. The control unit 60 also may monitor the rate and level of charge and discharge of the batteries 36 of the electrical storage 34 of the electrical system 30. The control unit 60 may monitor the voltage of the batteries 36 and the amperage and power being drawn from the batteries 36 by the components and peripherals. The control unit 60 may monitor the on/off status and the heat setting of the heater 40. The control unit 60 may monitor the on-off status and speed of the fan 52 of the air distributor 50. The control unit 60 may monitor the on/off status and other operational parameters of other peripherals 95 connected to the system to sterilize a physical space 10.

The control unit 60 is configured to control the operational status of the components and peripherals of the system to sterilize a physical space 10, including the fuel cell 20, the source of hydrogen 22, the electrical system 30 and its components, the heater 40, and the air distributor 50 and its components. The control unit 60 may send control commands to effect the operation.

For example, the control unit 60 may control the volume of hydrogen being generated by the source of hydrogen 22, the rate and volume of the hydrogen being supplied to the fuel cell 20, and the electrical power being generated by the fuel cell 20. The control unit 60 also may control the rate and level of charge and discharge of the batteries 36 of the electrical storage 34 of the electrical system 30. The control unit 60 may control the on/off status and the heat setting of the heater 40. The control unit 60 may control the on-off status and speed of the fan 52 of the air distributor 50. The control unit 60 may control the on/off status and other operational parameters of other peripherals 95 connected to the system to sterilize a physical space 10.

The control unit 60 is configured to log data about the operational status of the components and peripherals of the system to sterilize a physical space 10, including the fuel cell 20, the source of hydrogen 22, the electrical system 30 and its components, the heater 40, and the air distributor 50 and its components. The logged data may be stored locally in a local storage or remotely in a remote storage via the telecommunications network 12 or other network or direct connection.

The logged data may be saved permanently or temporarily as desired. Similarly, the logged data may be reported in electronic or physical reports either locally or remotely. The logged data values are important to verify the proper operation of the system to sterilize a physical space 10. They are also important to ensure that sufficient air temperatures were reached and were held for a sufficient time in a physical space being disinfected or sterilized to achieve a desired sterilization effect to eradicate pests and microorganisms.

The data about the operational status may comprise one or more of: an output level of power generated by the hydrogen fuel cell 20, an output level of the stored electrical power of the electrical system 30, the temperature of the heated air by the heater 40, an air temperature in one or more locations in the physical space obtained from one or more sensors in the physical space, an operating time period during which the heated air has been distributed into the physical space, a dwell time period during which the heated air is to continue to be distributed into the physical space, a location of the system, an indication of the operational status of one or more of the fuel cell 20, the electrical system 30, the heater 40, and the air distributor 50, and a time entry corresponding to the indication of the operational status of one or more of the fuel cell 20, the electrical system 30, the heater 40, and the air distributor 50.

The control unit 60 comprises a control panel 62 comprised of a display 64 and a plurality of information entry keys 66. The control panel 62, display 64, and information entry keys 66 provide a user interface to the system to sterilize a physical space 10. The control unit 60 is configured to display the data about the operational status of the various components and peripherals, including the fuel cell 20, the source of hydrogen 22, the electrical system 30 and its components, the heater 40, and the air distributor 50 and its components on the display 64.

Figure 7:
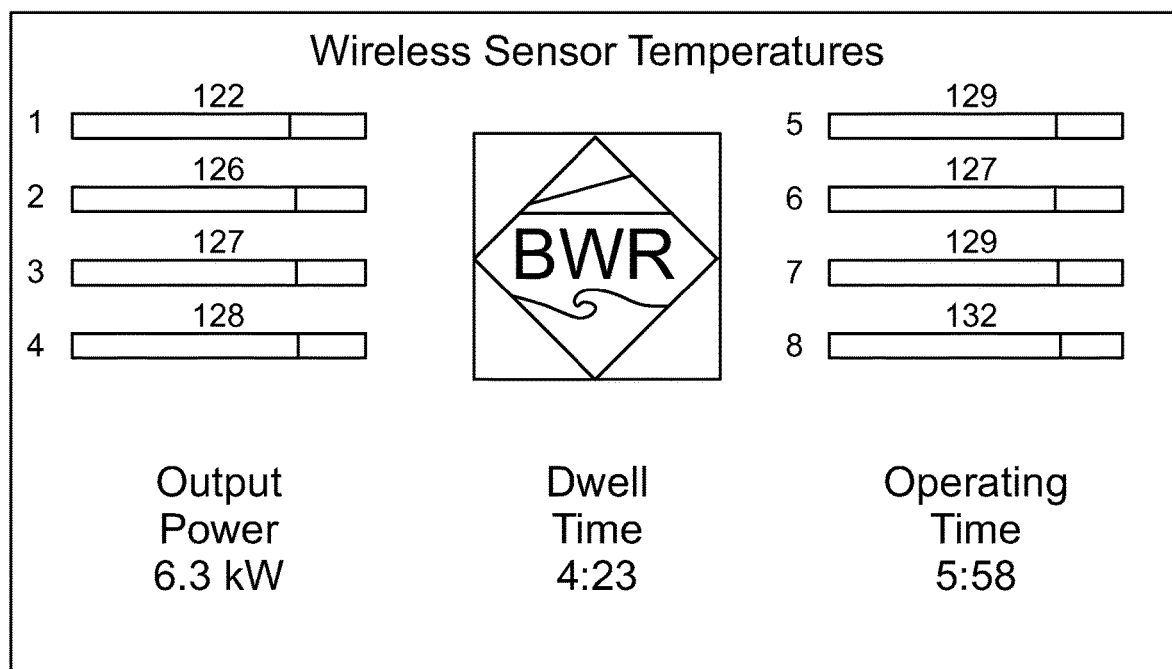
FIG. 7 is a diagram illustrating an example display of data on a control panel of a system to sterilize a physical space in accordance with an example embodiment.

For example, as illustrated in FIG. 7, at a given point in time, the control unit 60 may control the display 64 to display the output power of the system, e.g., "6.3 kW," the dwell time remaining for a disinfection or sterilization treatment, e.g., "4:23," and the operating time the system has been providing the disinfection or sterilization treatment, e.g., "5:58." The control unit 60 may control the display 64 to also display the air temperature data at various locations in the physical space being disinfected or sterilized as reported by wireless temperature sensors in the physical space, e.g., 122, 126, 127, 128, 129, 127, 129, and 132° F.

The control unit 60 is configured to receive information for controlling the operation of the various components and peripherals of the system to sterilize a physical space 10, including the fuel cell 20, the source of hydrogen 22, the electrical system 30 and its components, the heater 40, and the air distributor 50 and its components via the information entry keys 66. The control unit 60 is also configured to receive information for controlling the operation of the various components and peripherals via the mobile device 16 over the telecommunications network 12 or via another suitable network or direct connection.

The control unit 60 is configured to control the operation of the various components and peripherals of the system to sterilize a physical space 10, including the fuel cell 20, the source of hydrogen 22, the electrical system 30 and its components, the heater 40, and the air distributor 50 and its components based on the information received via the information entry keys 66. The control unit 60 is also configured to control the operation of the various components and peripherals based on information received via the mobile device 16 over the telecommunications network 12 or via another suitable network or direct connection.

If desired, a telemetry unit 68 may also be included in the system to sterilize a physical space 10. If included, the telemetry unit 68 is electrically coupled to the electrical system 30 and via the electrical system 30 to hydrogen fuel cell 20. The telemetry unit 68 receives and is powered by the stored power from the electrical storage 34 of the electrical system 30, and more particularly the batteries 36. The telemetry unit 68 is in communication with the control unit 60 via one or more suitable wired or wireless network or direct connections. The telemetry unit 68 is operable to communicate wirelessly with various sensors in the physical space to be disinfected or sterilized and to communicate sensor data received from the sensors to the control unit 60. For example, the telemetry unit 68 may receive temperature data from a plurality of temperature sensors positioned at various locations in the physical space. The telemetry unit 68 may also comprise its own sensors and communicate sensor data from its own sensors to the control unit. For example, the telemetry unit may include a temperature sensor to provide ambient temperature data at the system to sterilize a physical space 10. The telemetry unit 68 also may include a GPS transceiver to provide location information for the system to sterilize a physical space 10.

K. Portable Housing

All of the components of the system to sterilize a physical space 10, including source of hydrogen 22, the fuel cell 20, the electrical system 30, the heater 40, and the air distributor 50, can be and preferably are mounted to a portable housing 100. More preferably, each of the components is entirely or partially disposed within the portable housing 100.

Preferably, the portable housing 100 comprises a mobile cart 101 having wheels 102 and handles 103. These enable the system to sterilize a physical space 10 to be easily handled and to be easily transported to and set up in a hotel room, restaurant or other physical space to be disinfected or sterilized. Further, once that physical space has been treated, the system to sterilize a physical space 10 can be easily removed and transported to another physical space in the same or different premises.

Mounting and/or disposing all of the components of the system to sterilize a physical space 10 to and within the mobile cart 101 allows easy transport of the system into rooms or other physical spaces to be treated. In addition, since the system is portable and self-contained, it eliminates the need to locate the system or any component of the system outside of the physical space to be treated. The system and its operation are thus discrete and unobtrusive, and unlikely to draw any unwanted attention.

The portable housing 100 comprising the mobile cart 101 includes an electrical connection 39. The electrical connection 39 is electrically coupled to the electrical system 30, more particularly to the electrical storage 34 of the electrical system 30, and still more particularly to the battery 36 of the electrical storage 34. The electrical connection 39 is electrically coupled via the electrical system 30 to the hydrogen fuel cell 20. Although a single electrical connection 39 is referred to for ease of description herein, those skilled in the art will appreciate that a plurality of electrical connections 39 may be and preferably are included in the system and the reference to electrical connection 39 in the singular is meant to encompass and not to exclude the plural.

The electrical connection 39 is adapted to receive the stored electrical power from the electrical storage 34 of the electrical system 30, and more particularly the batteries 36, and to provide the stored electrical power for use outside the portable housing 100 to power peripherals and sensors connected to the electrical connection 39. The electrical connection 39 can supply power for peripherals and sensors requiring either AC or DC power, consistent with the description of the electrical system 30 above.

Figure 3:
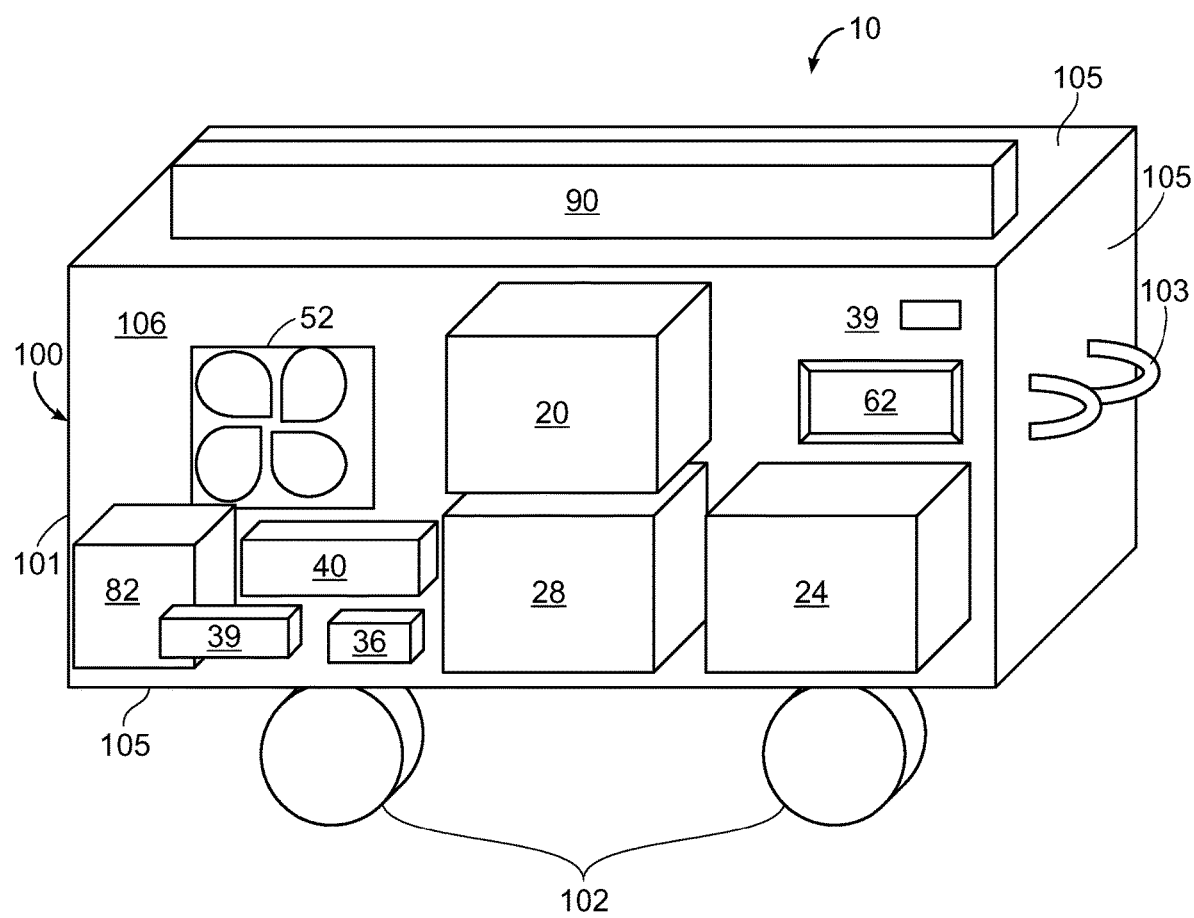
FIG. 3 is a stylized partial cutaway view of a portable housing, comprising a mobile cart with wheels, illustrating an example arrangement of components of a system to sterilize a physical space in accordance with an example embodiment.

The mobile cart 101 has top, bottom, front, back, and side walls 105 with exterior surfaces. The walls 105 enclose and define an interior space 106. The various components of the system to sterilize a physical space 10 may be arranged on the exterior surfaces of the walls 105 and within the interior space 106 of the mobile cart 101 in a number of ways. One example arrangement is illustrated in FIG. 3. Another example arrangement is illustrated in FIGS. 4-6.

In the example arrangement of FIG. 3, essentially all of the components of the system to sterilize a physical space 10 are disposed entirely within the interior space 106 of the mobile cart 101 except the filter 90, control panel 62, and electrical connections 39. These components are mounted on or are at least accessible through the exterior surfaces of the walls 105 of the mobile cart 101. The filter 90 is mounted on or exposed through the exterior surface of the top wall 105 so that the heated air from the heater 40 and air distributor 50 can flow through the filter 90 and be distributed into the physical space to be disinfected or sterilized. The control panel 62 is mounted on the exterior surface of a front wall 105 so that the display 64 and information entry keys 66 are accessible to a user. Similarly, the electrical connections 39 are mounted on or are exposed through the exterior surface of the front wall 105 to enable users to make electrical connections with peripherals that are remote from or external to the mobile cart 101, some examples of which are described further below.

Figure 4:
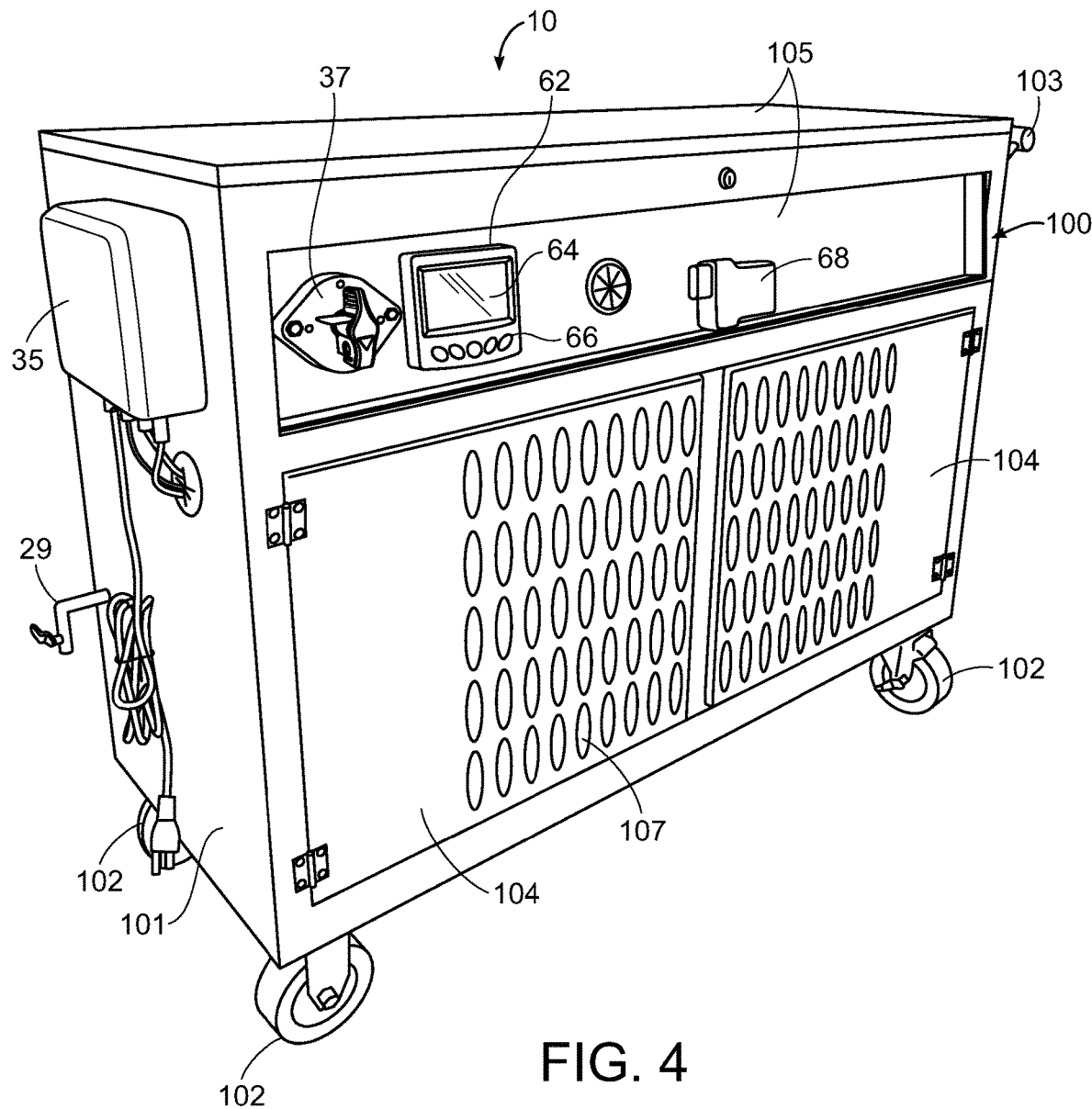
FIG. 4 is a front perspective view of a portable housing, comprising a mobile cart with wheels, illustrating several externally-mounted or accessible components of a system to sterilize a physical space in accordance with an example embodiment.
Figure 5:
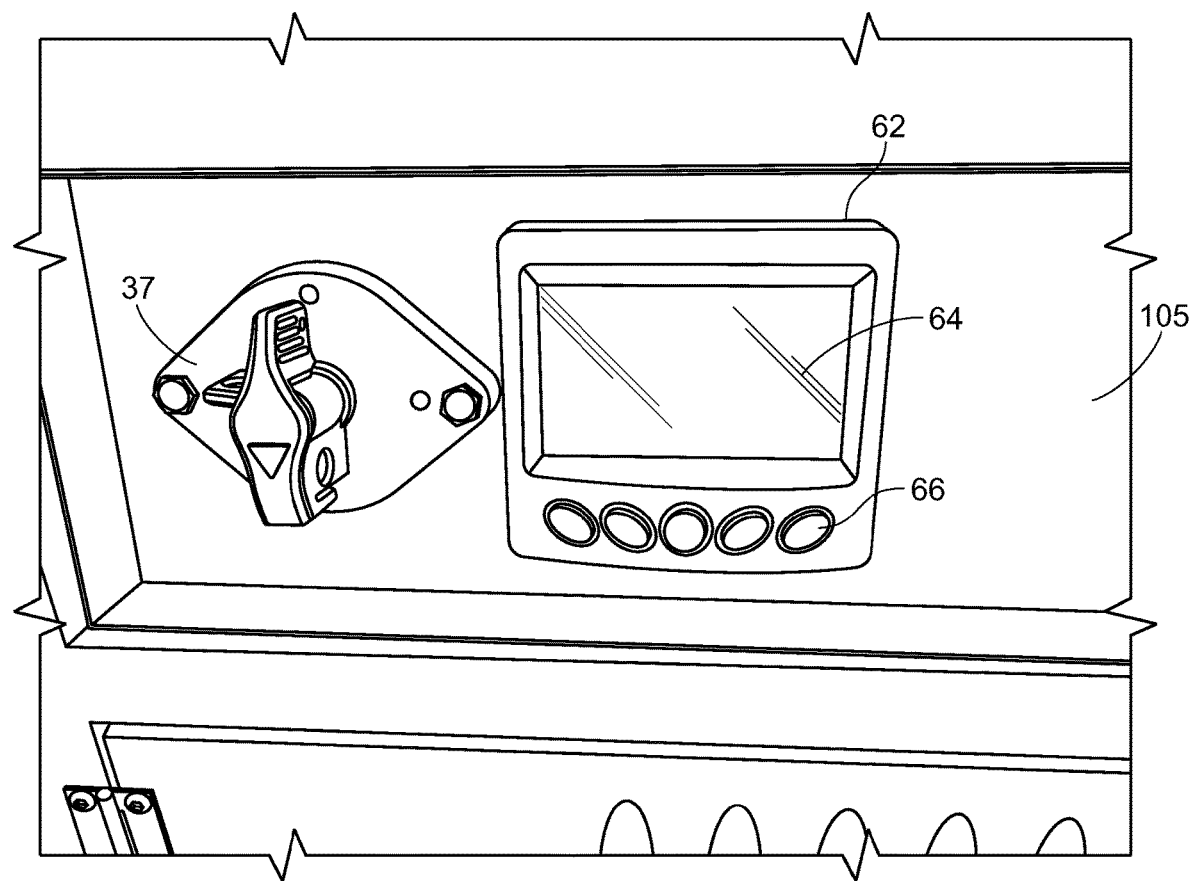
FIG. 5 is an enlarged view of a portion of the portable housing shown in FIG. 4, illustrating in further detail an electrical disconnect switch and a control panel of a system to sterilize a physical space in accordance with an example embodiment.
Figure 6:
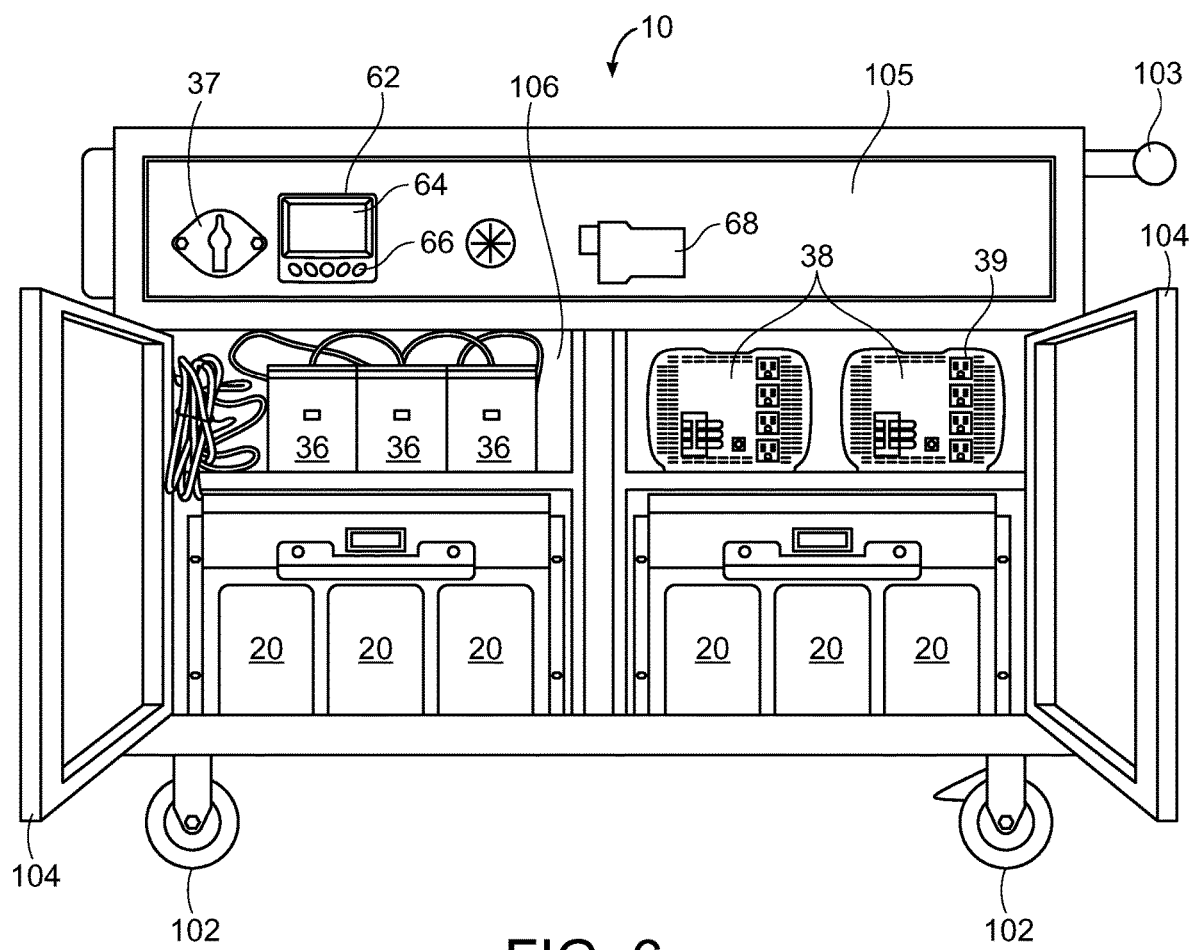
FIG. 6 is a front view of a portable housing, comprising a mobile cart with wheels, with access doors open illustrating an example arrangement of components of a system to sterilize a physical space in accordance with an example embodiment.

In the example arrangement of FIGS. 4-6, the exterior surface of the front wall 105 of the mobile cart 101 comprises hinged doors 104. The doors 104 are operable to be opened and closed. When the doors 104 are closed, the doors 104 and walls 105 of the mobile cart 101 enclose the interior space 106 of the mobile cart 101. When the doors 104 are open, the interior space 106 is exposed and accessible through the front wall 105. Vents 107 in the doors 104 allow air flow into and out of the interior space 106 and provide heat dissipation.

In this example arrangement, the electrical disconnect switch 37, the control panel 62 with display 64 and information entry keys 66, and the telemetry unit 68 are mounted to the portable housing 100 of the mobile cart 101 in a manner in which each is exposed and accessible by a user on or through the front wall 105 of the mobile cart 101. The hydrogen purge line and valve 29 extends from the interior space 106 of the portable housing 100 of the mobile cart 101 to the exterior through a side wall 105, where it accessible by a user. The battery charger 37 is also mounted on the side wall 105 where it is accessible by a user.

The other components of the system are mounted to and/or disposed within the interior space 106 of the portable housing 100 of the mobile cart 101. These include fuel cells 20, batteries 36, and inverters 38, which are visible, and the source of hydrogen 20, heater 40, air distributor 50, control unit 60, and filter 90, which are obscured from view.

L. UV Light Source

A UV light source 70 may be used as a peripheral in combination with the system to sterilize a physical space 10 to provide a particularly effective system for eradicating microorganisms in a room or other physical space to be disinfected or sterilized. In addition, UV light source 70 may help in eliminating allergens and undesirable odors from the physical space.

Although the UV light source 70 is referred to in the singular for ease of description herein, those skilled in the art will appreciate that a plurality of UV light sources 70 may be and likely will be used in combination with the system 10 to disinfect or sterilize a physical space, depending on the physical and other characteristics of the physical space. Therefore, the reference to UV light source 70 in the singular is meant to encompass and not to exclude the plural.

The use of UV light, such as (but not limited to) UVC, has been found to be effective in killing microorganisms. Accordingly, positioning one or more UV light sources in a room or other physical space to be disinfected or sterilized, in combination with applying heat to the physical space as described herein, provides a particularly effective way to eradicate microorganisms in the physical space, including microorganisms that may be resistant to eradication from heat alone.

The use of UVC for sterilization has been found to be particularly effective, as the United States Health and Human Services reports that UVC treatment is equally effective to multidrug-resistant microorganisms as to treatment of wild-type microorganisms that are not resistant to chemical treatments. UVC spans the ultraviolet spectrum from 200-280 nm, with 262 nm being the peak germicidal wavelength. Thus, UV light sources that irradiate in the UVC spectrum are preferred.

The UV light source 70 is adapted to be electrically coupled or connected to the electrical connection 39 of the portable housing 100. When electrically connected to the electrical connection 39, the UV light source 70 is electrically coupled via the electrical connection 39 to the electrical system 30, more particularly to the power conditioner 32 and electrical storage 34 of the electrical system 30, and still more particularly to the battery 36 of the electrical storage 34 of the electrical system 30. The UV light source 70 is also electrically coupled via the electrical system 30 to the hydrogen fuel cell 20.

The UV light source 70 is adapted to receive and be powered by the stored electrical power from the electrical storage 34 of the electrical system 30, and more particularly the batteries 36. The UV light source may be DC or AC powered consistent with the description of the electrical system 30 above. When electrically connected to the electrical connection 39 and positioned in a physical space to be disinfected or sterilized, the UV light source is operable to provide UV light in the physical space for treating against microorganisms. The application of UV light in the physical space may also help to eliminate allergens and odors.

The UV light source 70 may be connected to and be in communication with the control unit 60 via one or more suitable wired or wireless network or direct connections. The UV light source 70 may communicate operational status, such as off/on information to the control unit 60. The UV light source 70 also may receive and respond to control commands from the control unit 60, including commands to turn on and off.

M. Aerosol Dispenser

An aerosol dispenser 80 also may be used as a peripheral in combination with the system to sterilize a physical space 10 to help in eliminating allergens and undesirable odors from the physical space.

Although the aerosol dispenser 80 is referred to in the singular for ease of description herein, those skilled in the art will appreciate that a plurality of aerosol dispenser each dispensing the same or a different aerosol may be used in combination with the system to disinfect or sterilize a physical space 10, depending on the physical and other characteristics of the physical space, and the particular allergens and odors desired to be treated. Therefore, the reference to aerosol dispenser 80 in the singular is meant to encompass and not to exclude the plural.

The aerosol dispenser 80 typically will comprise a tank 82, a pump, and an aerosol dispersal element. Depending on the chemical content of the aerosol, the aerosol may be used to treat odors, treat allergens, and/or assist in the disinfection or sterilization process. An aerosol may be used for disinfection purposes such as by creating an aerosol with hydrogen peroxide, or to provide a specific fragrance based on the personal preference of the user or operator of the system to sterilize a physical space 10.

The aerosol dispenser 80 is adapted to be electrically coupled or connected to the electrical connection 39 of the portable housing 100. When electrically connected to the electrical connection 39, the aerosol dispenser 80 is electrically coupled via the electrical connection 39 to the electrical system 30, more particularly to the power conditioner 32 and electrical storage 34 of the electrical system 30, and still more particularly to the battery 36 of the electrical storage 34 of the electrical system 30. The aerosol dispenser 80 is also electrically coupled via the electrical system 30 to the hydrogen fuel cell 20.

The aerosol dispenser 80 is adapted to receive and be powered by the stored electrical power from the electrical storage 34 of the electrical system 30, and more particularly the batteries 36. The aerosol dispenser 80 may be DC or AC powered consistent with the description of the electrical system 30 above. When electrically connected to the electrical connection 39 and positioned in a physical space to be disinfected or sterilized, the aerosol dispenser is operable to dispense an aerosol into the physical space for disinfection and deodorization. The application of aerosol in the physical space may also help to eliminate allergens.

The aerosol dispenser 80 may be positioned at one or more locations in a room or other physical space to be disinfected or sterilized. Alternatively, the aerosol dispenser 80 may be mounted to the portable housing 100 of the mobile cart 101. Also alternatively, an aerosol dispenser 80 may be mounted to the portable housing 100 while other aerosol dispensers 80 may be positioned at one or more locations in the physical space. When multiple aerosol dispensers 80 are used, each aerosol dispenser 80 may provide the same or a different aerosol depending on the allergens and odors being treated against.

The aerosol dispenser 80 is connected to and in communication with the control unit 60 via one or more suitable wired or wireless network or direct connections. The aerosol dispenser 80 communicates operational status information to the control unit 60, such as the on/off state of the aerosol pump, the volume or pressure of aerosol in the aerosol tank 82, and/or the volume and type of aerosol dispensed during a given disinfection or sterilization treatment. The aerosol dispenser 80 is also controlled by the control unit 60 and may receive and respond to control commands from the control unit 60. Such commands might include to operate the aerosol pump to dispense a certain volume and type of an aerosol, or to dispense an aerosol for a given time, during a disinfection or sterilization treatment.

N. Other Peripherals

Other peripherals 95 also may be used in combination with the system to sterilize a physical space 10 to help in disinfecting or sterilizing a room or other physical space. For example, other peripherals 95 may comprise one or more of a fan, a sensor, and a light source. Various of the other peripherals 95 may be positioned at various locations in a room or other physical space to be disinfected or sterilized. Alternatively, one or more other peripherals 95 may be mounted to the portable housing 100 of the mobile cart 101. For example, one or more fans may be positioned in the physical space to help distribute and circulate the heated air distributed by the air distributor 50. One or more temperature sensors may be positioned at various locations in the physical space and report the air temperature at the sensor's location to the control unit 60. One or more light sources may be positioned in the physical space to illuminate the physical space in the event the physical space does not have its own source of illumination.

The other peripherals 95 are adapted to be electrically coupled or connected to the electrical connection 39 of the portable housing 100. When electrically connected to the electrical connection 39, the other peripherals 95 are electrically coupled via the electrical connection 39 to the electrical system 30, more particularly to the power conditioner 32 and electrical storage 34 of the electrical system 30, and still more particularly to the battery 36 of the electrical storage 34 of the electrical system 30. The other peripherals 95 are also electrically coupled via the electrical system 30 to the hydrogen fuel cell 20.

The other peripherals 95 may be adapted to receive and be powered by the stored electrical power from the electrical storage 34 of the electrical system 30, and more particularly the batteries 36. The other peripherals 95 may be DC or AC powered consistent with the description of the electrical system 30 above. Alternatively, for example where the other peripherals 95 comprise sensors, the sensors may have their own power sources and may not require operating power from the electrical system 30.

The other peripherals 95 may be connected to and be in communication with the control unit 60 via one or more suitable wired or wireless network or direct connections. The other peripherals 95 may communicate operational status information and/or data to the control unit 60. For example, other peripherals 95 comprising electronically controlled fans may communicate operational status such as on/off status and fan speed to the control unit 60. Other peripherals comprising temperature sensors may communicate temperature data to the control unit 60 on a continuous or demand basis. The other peripherals 95 also may be controlled by the control unit 60 and may receive and respond to control commands from the control unit 60. Where the other peripherals are electronically-controlled fans, such commands might include an on/off command or a command to change fan speed. Where the other peripherals are lights, such commands might include an on/off command and a dim command. Where the other peripherals are sensors, the commands might include a command to transmit data.

O. Operation of Preferred Embodiment

In an example use of the system to sterilize a physical space 10, the mobile cart 101 containing the components of the system is transported to a room or other physical space to be disinfected or sterilized. If UV lights 70, aerosol dispensers 80, and/or other peripherals 95 are to be used, they are positioned in the physical space as desired. If sensors, for example temperature sensors are to be used, they are also positioned in the physical space as desired. To the extent the UV lights 70, aerosol dispensers 80, other peripherals 95 and/or sensors require power to operate, they are connected to the electrical connections 39 on the mobile cart 101.

Preferably the batteries 36 will have been previously charged by the electrical power generated by the hydrogen fuel cell 20 and/or the battery charger 35 so that they hold sufficient stored electrical power to power the components and peripherals of the system to perform the desired disinfection or sterilization treatment. However, if necessary, the system operator may cause the hydrogen fuel cell 20 and/or the battery charger 35 to operate to charge the batteries 36 in place before the operator initiates the disinfection or sterilization treatment.

The system operator powers up the system, including the control unit 60 and control panel 62. Using the information entry keys 66 of the control panel 62, the operator enters the parameters for the disinfection or sterilization treatment to be carried out on the physical space. Alternatively, the operator may enter the parameters remotely using the mobile device 16. For example, the operator can enter a temperature to which the physical space is to be heated to achieve a desired sterilization effect, such as eradicating insects or organisms. The operator can also enter a dwell time for which that temperature is to be maintained in the physical space. If desired, the operator can enter other control parameters such as a fan speed for the air distributor 50. The operator then enters a command for the control unit 60 to initiate the disinfection or sterilization treatment in accordance with the entered parameters.

The operator can also enter instructions on the control panel 62 or using the mobile device 16 to activate and control the UV light sources 70, the aerosol dispensers 80, and other peripherals such as remote fans, if they are being used. For example, the operator can instruct the control unit 60 to activate one or more of the UV light sources 70 immediately, at a specified time, and/or for a specified period of time. The operator can also instruct the control unit 60 to control one or more aerosol dispensers 80 to dispense a specified amount of one or more types of aerosol immediately, or at specific times during the disinfection or sterilization treatment.

During the disinfection or sterilization treatment, it is preferable for the physical space to be closed if possible to help maintain the temperature in the space at the specified level. During the treatment, the control unit 60 automatically monitors the temperature level and can control and alter the operation of the heater 40 and air distributor 50 to maintain the specified temperature level. The control unit 60 also monitors the other system components and peripherals and logs data about the operational status of the system components and peripherals.

While the disinfection or sterilization process is on-going, the operator can also monitor the status on the display 64 of the control panel 62. The operator can, if desired or necessary, override the control unit 60 automatic operation of the treatment be entering commands on the control panel 62 using the information entry keys 66. In an emergency, for example, the operator can shut down power to the system components and peripherals by manually operating the electrical disconnect switch 37 on the mobile cart 101.

When the dwell time specified by the operator elapses, the control unit 60 automatically controls the system components to stop the disinfection or sterilization process. The operator may then remove the UV light sources, 70, aerosol dispensers 80, sensors, and other peripherals 95, shut down the system, and transport the mobile cart 101 to another location in the same or different premises having a physical space to be treated.

Any and all headings are for convenience only and have no limiting effect. Unless otherwise defined, all technical and scientific terms used herein have the same meaning as commonly understood by one of ordinary skill in the art to which this invention belongs. Although specific terms are employed herein, they are used in a generic and descriptive sense only and not for purposes of limitation. All publications, patent applications, patents, and other references mentioned herein are incorporated by reference in their entirety to the extent allowed by applicable law and regulations.

The data structures and code described in this detailed description are typically stored on a computer readable storage medium, which may be any device or medium that can store code and/or data for use by a computer system. This includes, but is not limited to, magnetic and optical storage devices such as disk drives, magnetic tape, CDs (compact discs), DVDs (digital video discs), and computer instruction signals embodied in a transmission medium (with or without a carrier wave upon which the signals are modulated). For example, the transmission medium may include a telecommunications network, such as the Internet.

At least one embodiment of the system to sterilize a physical space is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention. These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer-readable program code or program instructions embodied therein, the computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks. Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

The system to sterilize a physical space may be embodied in other specific forms without departing from the spirit or essential attributes thereof, and it is therefore desired that the present embodiment be considered in all respects as illustrative and not restrictive. Many modifications and other embodiments of the system to sterilize a physical space will come to mind to one skilled in the art to which this invention pertains and having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although methods and materials similar to or equivalent to those described herein can be used in the practice or testing of the system to sterilize a physical space, suitable methods and materials are described above. Thus, the system to sterilize a physical space is not intended to be limited to the embodiments shown, but is to be accorded the widest scope consistent with the principles and features disclosed herein.

What is claimed is:

1. A system for sterilizing a physical space, comprising:
a hydrogen fuel cell adapted to receive hydrogen from a source of hydrogen, wherein the hydrogen fuel cell is operable to use the hydrogen for generating electrical power;
an electrical system adapted to receive the electrical power, wherein the electrical system comprises an electrical storage for holding stored electrical power, wherein the electrical system is operable to store the electrical power in the electrical storage, and wherein the electrical system is operable to provide the stored electrical power for use outside the electrical system;
a heater adapted to receive the stored electrical power, wherein the heater is operable to produce heated air at a temperature sufficient to achieve a desired sterilization effect;
an air distributor adapted to receive the stored electrical power, and wherein the air distributor is operable to distribute the heated air into a physical space; and
a control unit in communication with the hydrogen fuel cell and the electrical system, the control unit configured to:
monitor an operational status of the hydrogen fuel cell and the electrical system; and
control the operation of the hydrogen fuel cell and the electrical system.

2. The system of claim 1, wherein the source of hydrogen comprises a tank containing compressed hydrogen.

3. The system of claim 1, wherein the source of hydrogen comprises a liquid feedstock and a reformer adapted to receive the liquid feedstock, wherein the reformer is operable to produce hydrogen locally from the liquid feedstock.

4. The system of claim 1, further comprising a mobile cart, wherein the hydrogen fuel cell, the electrical system, and the heater are mounted to the mobile cart.

5. The system of claim 1, wherein the hydrogen fuel cell is nearly silent while generating the electrical power and has an energy efficiency of at least about 50%.

6. The system of claim 1, wherein the electrical system comprises a power conditioner comprising electrical circuits operable to filter the electrical power.

7. The system of claim 1, wherein the electrical storage comprises a battery.

8. The system of claim 1, wherein the desired sterilization effect comprises killing one or more insects.

9. The system of claim 8, wherein the temperature sufficient to achieve a desired sterilization effect is a temperature between about 120° F. and 140° F.

10. The system of claim 1, wherein the desired sterilization effect comprises killing one or more microorganisms.

11. The system of claim 1, further comprising an electrical connection adapted to receive the stored electrical power and to provide the stored electrical power for use by one or more electrical components.

12. The system of claim 11, comprising a peripheral adapted to be coupled to the electrical connection to receive the stored electrical power, and wherein the peripheral comprises one or more of a fan, a sensor, and a light source.

13. The system of claim 11, comprising a UV light source adapted to be coupled to the electrical connection and to receive the stored electrical power, and wherein the UV light source is operable to provide UV light in the physical space for treating against microorganisms.

14. The system of claim 1, wherein the control unit is in communication with the heater and the air distributor, and wherein the control unit is configured to:
monitor the operational status of the heater and the air distributor; and
control the operation of the heater and the air distributor.

15. The system of claim 1, wherein the control unit is adapted to receive the stored electrical power, wherein the control unit is in communication with the heater and the air distributor, and wherein the control unit is configured to:
monitor the operational status of the heater and the air distributor; and
control the operation of the heater and the air distributor.

16. The system of claim 1, wherein the control unit comprises a control panel comprised of a display and a plurality of information entry keys, and wherein the control unit is configured to:
display the operational status on the display;
receive information for controlling the operation of the hydrogen fuel cell, the electrical system, the heater, and the air distributor via at least one of the plurality of information entry keys; and
control the operation of the hydrogen fuel cell, the electrical system, the heater, and the air distributor based on the information received via at least one of the plurality of information entry keys.

17. The system of claim 1, further comprising an aerosol dispenser adapted to receive the stored electrical power and operable to dispense an aerosol into the physical space for disinfection and deodorization.

18. The system of claim 1, comprising a filter adapted to receive the heated air from the air distributor and operable to remove particulates from the heated air.

19. A system for sterilizing a physical space, comprising:
a hydrogen fuel cell adapted to receive hydrogen from a source of hydrogen, wherein the hydrogen fuel cell is operable to use the hydrogen for generating electrical power;
an electrical system adapted to receive the electrical power, wherein the electrical system comprises an electrical storage for holding stored electrical power, wherein the electrical system is operable to store the electrical power in the electrical storage, and wherein the electrical system is operable to provide the stored electrical power for use outside the electrical system;
a heater adapted to receive the stored electrical power, wherein the heater is operable to produce heated air at a temperature sufficient to achieve a desired sterilization effect;
an air distributor adapted to receive the stored electrical power, and wherein the air distributor is operable to distribute the heated air into a physical space; and
a control unit in communication with the hydrogen fuel cell, the electrical system, the heater, and the air distributor, and is configured to:
monitor an operational status of the hydrogen fuel cell, the electrical system, the heater, and the air distributor; and
control the operation of the hydrogen fuel cell, the electrical system, the heater, and the air distributor.

20. A system for sterilizing a physical space, comprising:
a hydrogen fuel cell adapted to receive hydrogen from a source of hydrogen, wherein the hydrogen fuel cell is operable to use the hydrogen for generating electrical power;
an electrical system adapted to receive the electrical power, wherein the electrical system comprises a battery for holding stored electrical power, and wherein the electrical system is operable to provide the stored electrical power for use outside the electrical system;
an inverter adapted to receive the stored electrical power and to provide an AC electrical power for use by at least a fan and a UV light source;
a heater adapted to receive the stored electrical power, wherein the heater is operable to produce heated air at a temperature sufficient to achieve a desired sterilization effect;
an air distributor adapted to receive the stored electrical power, and wherein the air distributor is operable to distribute the heated air into a physical space; and
a control unit in communication with the hydrogen fuel cell, the electrical system, the heater, and the air distributor, the control unit comprising a control panel comprised of a display and a plurality of information entry keys, the control unit configured to:
monitor an operational status of the hydrogen fuel cell, the electrical system, the heater, and the air distributor;
display the operational status on the display;
receive information for controlling the operation of the hydrogen fuel cell, the electrical system, the heater, and the air distributor via at least one of the plurality of information entry keys; and
control the operation of the hydrogen fuel cell, the electrical system, the heater, and the air distributor based on the information received via at least one of the plurality of information entry keys;
wherein the operational status comprises an output level of the stored electrical power, the temperature of the heated air, an air temperature in one or more locations in the physical space, an operating time period during which the heated air has been distributed into the physical space, a dwell time period during which the heated air is to continue to be distributed into the physical space, a location of the system, an indication of the operational status of the hydrogen fuel cell, the electrical system, the heater, and the air distributor, and a time entry corresponding to the indication of the operational status of the hydrogen fuel cell, the electrical system, the heater, and the air distributor;
wherein the UV light source is operable to provide UV light in the physical space for treating against microorganisms.

* * * * *